US012746108B2

(12) United States Patent
Kershman et al.

(10) Patent No.: US 12,746,108 B2
(45) Date of Patent: Sep. 29, 2026

(54) COMPOSITIONS FOR ADMINISTERING A DOSE OF AN ACTIVE TO ANIMALS

(71) Applicant: Shear Kershman Laboratories, Inc., Chesterfield, MO (US)

(72) Inventors: Alvin Kershman, St Louis, MO (US); Jeff Shear, Bonita Springs, FL (US); Doreen Linze, Labadie, MO (US)

(73) Assignee: Shear Kershman Laboratories, Inc., Chesterfield, MO (US)

( * ) Notice: Subject to any disclaimer, the term of this patent is extended or adjusted under 35 U.S.C. 154(b) by 0 days.

(21) Appl. No.: 18/557,625

(22) PCT Filed: Apr. 13, 2022

(86) PCT No.: PCT/US2022/024514
§ 371 (c)(1),
(2) Date: Oct. 27, 2023

(87) PCT Pub. No.: WO2022/231839
PCT Pub. Date: Nov. 3, 2022

(65) Prior Publication Data

US 2024/0366353 A1 Nov. 7, 2024

Related U.S. Application Data

(60) Provisional application No. 63/181,911, filed on Apr. 29, 2021.

(51) Int. Cl.

| | |
|---|---|
| ***A61D 7/00*** | (2006.01) |
| ***A01K 7/02*** | (2006.01) |
| ***A61D 5/00*** | (2006.01) |
| ***A61K 8/34*** | (2006.01) |
| ***A61K 8/37*** | (2006.01) |
| ***A61Q 11/00*** | (2006.01) |

(52) U.S. Cl.
CPC .................. *A61D 7/00* (2013.01); *A01K 7/02* (2013.01); *A61D 5/00* (2013.01); *A61K 8/345* (2013.01); *A61K 8/375* (2013.01); *A61Q 11/00* (2013.01)

(58) Field of Classification Search
USPC ............................................................ 424/58
See application file for complete search history.

(56) References Cited

U.S. PATENT DOCUMENTS 4,752,481 A * 6/1988 Dokuzovic ............ A23G 4/068
426/651
6,331,291 B1 * 12/2001 Glace ..................... A61Q 11/00
424/53
9,173,941 B1 * 11/2015 Shear ................... A61K 31/573

* cited by examiner

*Primary Examiner* — Walter E Webb
(74) *Attorney, Agent, or Firm* — Dentons US LLP; Derek Auito

(57) ABSTRACT

A two phase system for administering a dose of an active to an animal having a liquid aqueous phase and a liquid oil phase, wherein the liquid oil phase has a dosage of at least one active, at least one oil and at least one surfactant, and the liquid oil phase has a density less than about 1.0 g/mL. The system is administered in an individual drinking container, such as a water bucket or water dish. The surfactant is non-water soluble and has an HLB of less than about 6.0. The oil phase adheres to tongue and mouth tissue of the pet or livestock that consumes it from the water bucket or water dish.

14 Claims, No Drawings

COMPOSITIONS FOR ADMINISTERING A DOSE OF AN ACTIVE TO ANIMALS

CROSS-REFERENCE TO RELATED APPLICATIONS

This application claims the benefit of provisional patent application 63/181,911 filed Apr. 29, 2021, which is hereby incorporated by reference, and of PCT application PCT/US22/24514 filed Apr. 13, 2022, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to providing a two phase system having a dosage of an active. More particularly the present invention is a two phase system having an aqueous phase and an oil phase, where the oil phase has a dosage of an active, wherein the oil phase has a density less than about 1.0 g/mL, and the system is administered to animals, such pets or livestock, in an appropriate individual drinking container such as a water bucket or dish.

Related Art

Therapeutic actives are administered to animals by a variety of routes. These routes include, for example, oral ingestion, topical application or parenteral administration. However, many oral compositions comprising active agents with a bitter or unpleasant taste are not well accepted by animals. Problems such as these often lead to low or sub-optimal efficacy and control of parasites. Antiparasitic actives have been administered to livestock by placing the active in the drinking water and/or food. The disadvantage with this known method of administering actives is that it is difficult to give the animal the correct dosage by these means.

Known pet products have been used for administering breath fresheners and dental treatments by adding the product to a pet water dish. These products are designed to have a single phase and be suspended or dissolved in water. It is difficult to provide a dosage of an active using the prior art products, because an animal may not lap up all the water, or, alternatively, may splash and spill some of its water, losing part of the dosage.

Examples of known products are described in the references listed below, which are hereby incorporated by reference. US20110038929A1, US20150209263, and WO2005063184 disclose breath fresheners added to pet drinking bowls. WO2005066177 discloses an antiparasitic that can be added to drinking water or food. None of the above cited references disclose the two phase system claimed herein.

SUMMARY OF THE INVENTION

The present invention is a two phase system comprising an aqueous phase and an oil phase in an appropriate individual water container, such as a pet water dish or a livestock water bucket, wherein the oil phase comprises at least one surfactant, at least one oil, and at least one active. The surfactant to lipid weight ratio is from about 1:1 to about 10:1. Preferably the surfactant to lipid weight ratio is from about 1:1 to about 3:1. The total of the at least one surfactant and the at least one oil in the oil phase is from 60 to 100 wt. %. The at least one surfactant comprises a non-water soluble surfactant having an HLB number of less than about 6. Optionally, the oil phase also includes at least oil, at least one surfactant and water. Further optionally, the oil phase includes at least one oil, at least one surfactant, water and at least one humectant. The oil phase has a density of less than about 1.0 g/mL, and, when consumed, adheres to wet tongue and mouth tissue.

The present invention further comprises a method of administering an active to an animal. The method includes adding water to an individual drinking container suitable for the animal, and adding an oil phase to the water of the drinking container. The oil phase comprises at least one surfactant, at least one oil, and at least one active. The weight of the surfactant to lipid ratio is from about 1:1 to about 10:1, and the total of the at least one surfactant and the at least one oil in the oil phase is from 60 to 100 wt. %. The at least one surfactant comprises a non-water soluble surfactant having an HLB number of less than about 6. The two phases are administered to the animal.

The invention further includes adding an amount of the oil phase that contains a measured dose of the active to individual animal feed to deliver the desired dosage to the animal.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

The present system provides a product and a method to deliver a measured dose of an active to an animal that drinks water from an individual container. For example, a pet that laps water from a water bowl or livestock that drinks from a water bucket could consume a measured dose of an active. Prior art products and methods failed to provide such a system, in that the product was dissolved or dispersed in the water, and when the pet lapped the water, it either spilled some dosage or did not consume all of the water in the dish. The present product and method provides a dosage that, because it contains oil and a surfactant having a HLB of about 6 or less, is a separate phase from the water, and because it is less dense than water, floats on top of the water phase. The pet's tongue or the livestock's tongue, when lapping from the water dish, touches the oil phase floating on top of the water. The oil phase of the present invention adheres to the wet tissue of the tongue and mouth of the pet or livestock and is consumed entirely by the pet or livestock. When the administered active is a breath freshener, the freshening effect can last from about 2 to 4 hours.

The oil phase contains at least one oil or petroleum distillate, at least one surfactant, and at least one active. The at least one oil may also comprise partially or completely the at least one active, as an active may also be an oil. Alternatively, the active is not an oil.

The surfactant is preferably a non-water soluble surfactant having an HLB number of less than about 6, and includes emulsifiers. Examples of suitable surfactants include oleic acid, acetylated monoglycerides, glycerol dioleate, sorbitan tristearate, glycerol monoleate, acetylated monoglycerides and various combinations of these. A preferred surfactant is commercially sold as ATMOS® 300K, and is a combination of mono- and di-glycerides made from edible food sources and propylene glycol with an HLB of about 2.8. Another suitable surfactant for the present invention is sold as LUCRAFOAM E 100 in Europe and as DEFOSPUM E 100 in the United States, and is a Mono-, Di- and Triglyceride of fatty acids with an HLB number of less than about 6. More preferably, the HLB is less than about 3.0.

In an embodiment, the oil phase contains a second surfactant that has an HLB number of about 6. The preferred surfactant is glyceryl monostearate and has an HLB of about 5.8. In an embodiment, the weight ratio of ATMOS®300K surfactant to weight of the glyceryl monostearate is in the range of about 5:1 to 10:1. The surfactant is present in the oil phase in the amount of about 40 to 60 wt. %, and the oil is present from about 10 to 40 wt. %.

The oil suitable for the oil phase is typically liquid at room temperature, and is compatible with the food grade or pharmaceutical grade applications. Such oils include essential oils, plant oils, such as vegetable oil, corn oil, canola oil, coconut oil, castor oil or olive oil, shea butter, and animal fats. Preferred oils include grapeseed oil and peppermint oil. The oils include petroleum distillates, such as petrolatum and mineral oil. Mixtures of oils are also contemplated in the present invention. Sta-Set RCS™ is a blend of rapeseed, cottonseed and soybean stearines that is typically used in <10 wt. % of the oil phase. In a preferred embodiment, the surfactant and the oil are present in the oil phase in a weight ratio of about 10:1 to 1:1 surfactant to oil. In a more preferred embodiment, the preferred weight ratio of surfactant to oil is in the range of about 3:1 to 1:1.

Optionally, the oil phase contains water and at least one humectant. Suitable humectants include, but are not limited to glycerin, lactic acid, polyols, propylene glycol, corn syrup, high fructose corn syrup (HFCS), including Cornsweet 55 (55 wt. % fructose, 24 wt. % water and 21 wt. % glucose) and Cornsweet 42 (42 wt. % fructose, 24. wt. % water and 34 wt. % glucose), and sorbitol. The preferred form of humectant is non-crystallizing liquid sorbitol (70 wt. % sorbitol in water). The at least one humectant is present in the oil phase from 1 to 40 wt. %. More preferably, the at least one humectant is present in the oil phase from about 1 to 10 wt. %.

The active delivered in the present system can be either a lipid soluble active, a water soluble active, or an active with limited solubility in either solvent. For lipid soluble actives, the system may not contain water or humectants in the oil phase, as they would not be needed to carry the active. For water-soluble actives, the oil phase will use water and humectants to carry the active into the oil phase. The oil phase can carry water and humectant in amounts that do not increase the density of the oil phase to about 1.0 g/mL or more.

Lipid soluble actives include praziquantel (anti-parasitic), moxidectin (anti-parasitic), omeprazole (for digestive issues), and pergolide (for pituitary issues). These actives are regularly and repeatedly administered to pets and livestock. It is very desirable to have a simple and convenient way of administering these actives. Lipid-soluble actives also include essential oils, such as peppermint oil, which impart breath-freshening properties.

Water soluble actives include antiplaque and anti-tartar actives. Additional antiplaque and anti-tartar actives include cetyl pyridinium chloride and related quaternary salts such as chlorhexidine; zinc salts such as zinc chloride and zinc sulfate monohydrate; stannous salts such as stannous chloride and stannous fluoride; and peroxides such as hydrogen peroxide and carbamide peroxide; sodium percarbonate; magnesium perphthalate; and sodium perborate.

A preferred range of wt. % of components of the oil phase are:

| | |
|---|---|
| Atmos ®-300 (surfactant) | 40-70 |
| Grapeseed oil | 10-40 |
| Peppermint oil | 0-2.0 |
| Optionally, water or water + Humectant | 1-40 |
| Active | 0-25 |

Examples of the Oil Phase of the Invention

| Ingredient | Weight (g) | wt. % |
|---|---|---|
| Example 1 - Breath Freshener for Dogs The Liquid Oil Phase | | |
| ATMOS ® 300K Surfactant | 34.98 | 69.96 |
| Expeller Pressed Grapeseed Oil | 14.92 | 29.84 |
| Peppermint Terpeneless Oil Active | 0.10 | 0.20 |
| Example 2 - Breath Freshener for Dogs The Liquid Oil Phase | | |
| ATMOS ® 300K Surfactant | 89.04 | 59.36 |
| Expeller Pressed Grapeseed Oil | 38.16 | 25.44 |
| Peppermint Terpeneless Oil Active | 0.30 | 0.20 |
| purified water (Distilled) | 11.25 | 7.50 |
| Humectant | 11.25 | 7.50 |

The ingredients were mixed together to form the oil phase, and stored in a closed, water-tight container. The system was prepared using a pet dish about half filled with water. The oil phase was measured and poured onto the water, where it formed a second phase and floated on top of the water. A dog was given the system, and it lapped up the oil, clearly enjoying the taste and mouth feel of the product. It drank all the liquid in the bowl. The system provided breath freshening properties, and peppermint could be smelled on the breath of the dog for hours after consumption.

Doses of 3 mL of Examples 1 and 2 were poured in a pet dish half filled with water. Both Examples floated on the water. Dogs drank and contacted the Examples. No dog showed any sign of discomfort. After the dogs drank, their breath was smelled after 30 minutes, after one hour, and then every hour. Good breath odor lasted for about 3 hours (one dog each for Example 1 and Example 2), and for 4 hours (one dog each for Example 1 and Example 2).

Example 3 - for Horses - Anti-parasitic
The Liquid Oil Phase

| Ingredient | Weight (g) | wt. % |
|---|---|---|
| ATMOS ® 300K Surfactant | 27.7420 | 50.44 |
| Grapeseed Oil | 15.6530 | 28.46 |

-continued

| Example 3 - for Horses - Anti-parasitic The Liquid Oil Phase | | |
|---|---|---|
| Ingredient | Weight (g) | wt. % |
| Sta-Set Oil | 3.6300 | 6.60 |
| Praziquantel Active | 6.8750 | 12.50 |
| Moxidectin Active | 1.1000 | 2.00 |

The ingredients were mixed together to form the oil phase, and stored in a closed, water-tight container. Horses naturally infected with cyathostomins (small strongyles) (+++) were dosed with Example 3 in two ways.

A first horse received Example 3 poured over drinking water (individual water cup system in a stable) at a dosage of 5 mL/250 kg. It took the horse a while to drink (ca. ½ hour), but after drinking the product was gone. Two days after application feces were collected and proven that the infection was gone (0 worms detected).

A second horse was dosed with Example 3 by mixing into its favorite food at a dosage of 5 mL/250 kg. The horse consumed it all immediately after it was put in front of him. Two days after application feces were collected and proven that the infection was gone (0 worms detected).

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A composition for oral administration to an animal, comprising;

at least one surfactant, at least one oil, and at least one active;

wherein the at least one surfactant and the at least one oil are present in a weight ratio of from about 1:1 to about 10:1 surfactant to oil;

wherein the total of the at least one surfactant and the at least one oil is from about 60 to 100 wt. %;

wherein one of the at least one surfactant comprises a non-water soluble surfactant having an HLB of about 6.0 or less, wherein the composition has a density of less than about 1.0 g/mL such that when the composition is added to water in a drinking container, the composition floats on the water; and wherein the composition adheres to wet tongue and mouth tissue of the animal when the animal drinks the water from the drinking container.

2. The composition of claim 1, wherein the at least one active is an oil soluble active.

3. The composition of claim 2, wherein the at least one active is an essential oil.

4. The composition of claim 1, further comprising at least one humectant.

5. The composition of claim 1, wherein the amount of active present in the composition is equal to one dose for the animal.

6. A method of administering an active to an animal, the method comprising:

adding a composition comprising at least one surfactant, at least one oil, and at least one active to an individual drinking container suitable for an animal:

wherein the at least one surfactant and the at least one oil are present in a weight ratio of from about 1:1 to about 10:1 surfactant to oil;

wherein the total of the at least one surfactant and the at least one oil is from 60 to 100 wt. %;

wherein the at least one surfactant comprises a non-water soluble surfactant having an HLB number of about 6 or less; and wherein the composition has a density of less than about 1.0 g/mL such that when the composition is added to water in the drinking container, the composition floats on the water; and wherein the composition adheres to wet tongue and mouth tissue of the animal when the animal drinks the water from the drinking container.

7. The method of claim 6, wherein the at least one active is present in the amount of one dosage for the animal.

8. The method of claim 7, wherein the at least one active is an essential oil.

9. The method of claim 6, wherein the composition further comprises at least one humectant.

10. A liquid oil composition comprising at least one surfactant, at least one oil, and at least one active;

wherein the at least one surfactant and the at least one oil are present in a weight ratio of from about 1:1 to about 10:1 surfactant to oil;

wherein the total of the at least one surfactant and the at least one oil is from about 60 to 100 wt. %;

wherein the at least one surfactant comprises a non-water soluble surfactant with an HLB of about 6.0 or less, wherein the composition has a density of less than about 1.0 g/mL such that when the composition is added to water in a drinking container, the composition floats on the water; and wherein the composition adheres to wet tongue and mouth tissue of the animal when the animal drinks the water from the drinking container.

11. The liquid oil composition of claim 10, wherein the composition further comprises at least one humectant.

12. The liquid oil composition of claim 11, wherein the at least one active includes antiplaque and anti-tartar actives.

13. The composition of claim 1 wherein the at least one active includes antiplaque and anti-tartar actives.

14. The method of claim 6, wherein the at least one active includes antiplaque and anti-tartar actives.

* * * * *